US008304583B2

(12) United States Patent
Miller et al.

(10) Patent No.: US 8,304,583 B2
(45) Date of Patent: Nov. 6, 2012

(54) HYDROGENATION OF ALIPHATIC DIALDEHYDES TO ALIPHATIC DIOLS

(75) Inventors: Glenn A. Miller, South Charleston, WV (US); Jeffrey S. Sawrey, Westford, MA (US); Christopher W. Derstine, Midland, MI (US)

(73) Assignee: Dow Global Technologies LLC

( * ) Notice: Subject to any disclaimer, the term of this patent is extended or adjusted under 35 U.S.C. 154(b) by 188 days.

(21) Appl. No.: 12/674,933

(22) PCT Filed: Aug. 21, 2008

(86) PCT No.: PCT/US2008/073800
§ 371 (c)(1),
(2), (4) Date: Jan. 13, 2011

(87) PCT Pub. No.: WO2009/035838
PCT Pub. Date: Mar. 19, 2009

(65) Prior Publication Data
US 2011/0098514 A1    Apr. 28, 2011

(51) Int. Cl.
*C07C 29/16* (2006.01)
(52) U.S. Cl. ........................................ 568/830; 568/831
(58) Field of Classification Search ................ 568/830, 568/831
See application file for complete search history.

(56) References Cited

U.S. PATENT DOCUMENTS

| 2,809,220 | A  | 10/1957 | Mertzweiller et al. |
| 4,401,834 | A  | 8/1983  | King |
| 5,059,710 | A  | 10/1991 | Abatjoglou et al. |
| 6,252,121 | B1 | 6/2001  | Argyropoulos et al. |
| 6,303,829 | B1 | 10/2001 | Kanel et al. |
| 6,307,110 | B1 | 10/2001 | Argyropoulos et al. |
| 6,350,923 | B1 | 2/2002  | Eller et al. |
| 6,680,414 | B2 | 1/2004  | Knoop et al. |
| 7,598,374 | B2 | 10/2009 | BeMiller et al. |
| 2007/0161829 | A1 | 7/2007 | Van Driessche |

FOREIGN PATENT DOCUMENTS

| GB | 653765    | 5/1948  |
| GB | 750144    | 12/1952 |
| JP | 1997301904 | 11/1997 |
| WO | 2009035838 | 3/2009  |

*Primary Examiner* — Sikarl Witherspoon

(57) ABSTRACT

A process of hydrogenating an aliphatic dialdehyde, preferably, a $C_6$-$C_{16}$ alicyclic dicarboxaldehyde, to form an aliphatic diol, preferably, a $C_6$-$C_{16}$ alicyclic diol, most preferably, cis/trans-(1,3)(1,4)-cyclohexanedimethanol. The process involves contacting one or more aliphatic dialdehydes in a liquid phase with hydrogen in the presence of a hydrogenation catalyst in a hydrogenation zone and in the presence of water in an amount equal to or greater than 10 weight percent, based on the weight of the total liquid feed to the hydrogenation. The alicyclic dicarboxaldehyde is preferably prepared via hydroformylation of an olefin with subsequent extraction of the alicyclic dicarboxaldehyde product from the hydroformylation product fluid.

19 Claims, No Drawings

US 8,304,583 B2

HYDROGENATION OF ALIPHATIC DIALDEHYDES TO ALIPHATIC DIOLS

CROSS-REFERENCE TO RELATED APPLICATION

This application is a 371 of PCT/US2008/073800 filed Aug. 21, 2008, which claims the benefit of U.S. Provisional Application Ser. No. 60/967,825, filed Sep. 7, 2007.

BACKGROUND OF THE INVENTION

This invention pertains to a process of hydrogenating aliphatic dialdehydes, preferably alicyclic dialdehydes, with hydrogen in the presence of a hydrogenation catalyst to prepare the corresponding aliphatic diols, preferably, alicyclic diols.

Aliphatic diols find utility as solvents and as intermediates in the preparation of industrially useful chemicals. Alicyclic diols, such as the cis/trans isomers of 1,3- and 1,4-cyclohexanediol, are known to be useful as solvents and as intermediates in the manufacture of plasticizers and detergents.

It is known that aldehydes can be catalytically reduced with hydrogen in the presence of a hydrogenation catalyst to form alcohols. Hydrogenation catalysts advantageously comprise at least one metal of Groups 6, 7, 8, 9, 10, 11, or 12 of the Periodic Table of the Elements, referenced as described hereinafter. The hydrogenation of aldehydes can be carried out continuously or batchwise in a gas or liquid phase. For the industrial production of alcohols via the hydrogenation of aldehydes obtained from hydroformylation of olefins ("OXO process"), preference is given to continuous gas or liquid phase processes using hydrogenation catalysts in a fixed bed. As used herein, the term "hydroformylation" refers to a process of contacting an olefinically-unsaturated compound characterized by at least one unsaturated carbon-carbon (C=C) double bond with carbon monoxide and hydrogen (synthesis gas or syngas) in the presence of a hydroformylation catalyst to obtain therefrom an aldehyde product characterized by a carboxaldehyde (formyl) substituent (—CH=O). Hydroformylation catalysts comprise a transition metal complexed to an organophosphorus ligand, advantageously, an organophosphite ligand, and preferably, a triorganomonophosphite or an organobisphosphite ligand.

High molecular weight aldehydes, that is, aldehydes having 6 or more carbon atoms (C6+), are preferably hydrogenated in the liquid phase, particularly, as the molecular mass and boiling point of such compounds are generally too high for a gas phase process. Hydrogenation in the liquid phase presents a disadvantage, however, in that owing to high concentrations of both aldehydes and alcohols the formation of high boilers is promoted via secondary reactions. In particular, aldehydes can undergo aldol reactions (addition and/or condensation) with alcohols to form unsaturated aldehydes (enals), hemiacetals and/or acetals. The hemiacetals and acetals can subsequently undergo elimination of water or alcohol, respectively, to form enol ethers, which under hydrogenation conditions form saturated ethers. Dialdehydes can undergo self-condensation to produce heavies, including dimers, trimers, and higher oligomers. All of the enal, hemiacetal, acetal, enol ether, and saturated ether by-products as well as self-condensation heavies are considered "heavies" and they reduce the yield of the desired alcohol.

The hydrogenation of high molecular weight aldehydes having 6 or more carbon atoms prepared via hydroformylation presents additional problems in liquid phase hydrogenation of the aldehydes to alcohols. Due to the high molecular weight of C6+ aldehyde products, the viscosity of such aldehydes can be unacceptably high, which consequentially increases difficulties in transporting and handling these aldehydes in a liquid phase. Moreover, hot spots might develop in an unacceptably viscous liquid phase leading to an increased production of heavies. Additionally, the aldehyde feed to the hydrogenation process, being obtainable from a hydroformylation process, disadvantageously can contain a low quantity of one or more organophosphite ligands and/or degradation products derived from the organophosphite ligand(s). These organophosphites or their degradation products are capable of binding and poisoning the hydrogenation catalyst. As a further disadvantage, the hydrogenation of di- and poly-carboxaldehydes generally results in increased formation of polymeric heavies (including dimers and trimers) and lactones, as compared with the hydrogenation of mono-carboxaldehydes. In addition, di- and poly-carboxyaldehydes can engage in intramolecular side reactions to form, for example, cyclic acetals and lactones.

In view of the above, an improvement in the liquid phase hydrogenation of aliphatic dialdehydes, preferably C6+ alicyclic dialdehydes derived from hydroformylation processes, is desirable in preparing the corresponding diols, preferably, C6+ alicyclic diols.

U.S. 2007/0161829 A1 discloses use of a controlled amount of water in a hydrogenation stage of an oxo product for the production of alcohols, which uses at least two reactors in series with a reduction in the amount of sulfur, chlorine and hydroformylation catalyst residues fed to the hydrogenator. A quantity of water from 0.5 to 3 weight percent, especially from 1 to 2 weight percent, is used based on the weight of the product injected into the hydrogenator.

U.S. Pat. No. 6,680,414B2 discloses a process of hydrogenating an aldehyde product derived from the hydroformylation of one or more $C_4$-$C_{16}$ olefins, such as dibutene. The hydrogenation is conducted in the presence of an excess of hydrogen, a Group 8 transition metal catalyst, and from 0.05 to 10 percent by weight of water so as not to form a separate aqueous phase.

U.S. Pat. No. 5,059,710 and U.S. Pat. No. 4,401,834 disclose pretreating a hydroformylation aldehyde product with water in a thermal treatment zone prior to hydrogenation. It is disclosed that water may be added to the hydrogenation in an amount from about 1 to 8 volume percent, based on the volume of aldehyde feed.

U.S. Pat. No. 2,809,220 discloses a vapor phase hydrogenation of aldehydes in the presence of hydrogen, a sulfurized hydrogenation catalyst, and added water vapor. The amount of water introduced into the hydrogenation zone is preferably from 1 to 10 moles water per mole acetal, or preferably from about 1 to 8 volume percent, based on the volume of aldehyde feed. In order to maintain the added water in a vapor phase, a large excess of hydrogen is employed (e.g., liquid feed rate from 0.25 to 2 v/v/h and hydrogen feed rate 5000-20,000 $ft^3$/barrel of feed)

SUMMARY OF THE INVENTION

In one aspect, this invention provides for hydrogenation of an aliphatic dialdehyde to prepare a corresponding aliphatic diol. Accordingly, the process of this invention comprises contacting one or more aliphatic dialdehydes (also referred to herein as "dicarboxaldehydes") in a liquid phase with hydrogen in the presence of a hydrogenation catalyst in a hydrogenation zone, and in the presence of water in an amount equal to or greater than 10 weight percent, based on the weight of the total liquid feed to the hydrogenation process. The contacting is conducted under reaction conditions sufficient to prepare the corresponding one or more aliphatic diols. As used herein, the phrase "total liquid feed to the hydrogenation process" refers to the total liquid feed fed to the hydrogenation zone including but not limited to total water feed and/or co-feed, any other solvent or diluent as may be used, the one or more aliphatic dicarboxaldehydes, any impurities and/or by-products present in the aliphatic dicarboxaldehyde(s) including but not limited to organophosphorus ligands, organophosphorus ligand degradation products, hemiacetals, acetals, lactones, and/or other heavies including dimers, trimers, and higher oligomers, and any recycle stream from the hydrogenation process including but not limited to unreacted aliphatic dicarboxaldehyde(s), aliphatic diol product(s), and any solvents, impurities, and byproducts present in the hydrogenation effluent stream.

The process of this invention converts an aliphatic dialdehyde or mixture thereof, preferably one or more $C_6$-$C_{16}$ alicyclic dialdehydes, to the corresponding aliphatic diol or mixture thereof, preferably, to the corresponding one or more $C_6$-$C_{16}$ alicyclic diols. In a preferred embodiment of this invention, a mixture of cis/trans isomers of 1,3- and 1,4-cyclohexane dicarboxaldehyde (hereinafter "cis/trans-(1,3) (1,4)-cyclohexane dicarboxaldehyde") is hydrogenated in a liquid phase to the corresponding mixture of cis/trans isomers of 1,3- and 1,4-cyclohexanedimethanol (hereinafter "cis/trans-(1,3)(1,4)-cyclohexane dimethanol"), which alcohol composition is useful in the manufacture of polyester resins or plasticizers. The process of this invention effectively reduces heavies, including byproduct hemiacetals, acetals, enol ethers, and other heavies that might otherwise be present as impurities in the aliphatic dialdehyde, and thereby increases the yield of desired aliphatic diol.

In addition to the above, the process of this invention may provide other beneficial effects, although the invention should not be limited by any discussion thereof. For example, the process of the invention is beneficially employed with high molecular weight aliphatic dialdehydes having 6 or more carbon atoms (C6+) that are typically viscous and difficult to handle. Water employed in the process of this invention lowers the viscosity of the high molecular weight dialdehyde(s) fed to the hydrogenation process, thereby rendering transportation and handling of the liquid dialdehyde(s) more acceptable. Moreover, water introduced into the hydrogenation process helps to dissipate heat of hydrogenation, thereby reducing the potential for hot spots that accelerate heavies formation. As a further advantage, organophosphite ligands or degradation products derived from organophosphite ligands, which can be present in the feed to the hydrogenation process, are hydrolyzed by water, thereby avoiding the binding of such organophosphites and organophosphite ligand degradation products to the hydrogenation catalyst with consequential poisoning of the catalyst.

In another aspect, this invention provides for the production of one or more aliphatic diols comprising:

(a) contacting in a hydroformylation zone an olefinically-unsaturated aliphatic aldehyde with carbon monoxide and hydrogen in the presence of a transition metal-organophosphorus ligand complex catalyst and, optionally, free organophosphorus ligand under hydroformylation conditions sufficient to prepare a hydroformylation product composition comprising one or more aliphatic dicarboxaldehydes, the transition metal-organophosphorus ligand complex catalyst, and optionally, free organophosphorus ligand;

(b) mixing in an extraction zone the hydroformylation product composition with water and, optionally, a nonpolar solvent under conditions sufficient to obtain by phase separation a nonpolar phase comprising the transition metal-organophosphorus ligand complex catalyst, optionally, free organophosphorus ligand, and optionally, the nonpolar solvent and a polar phase comprising water and the one or more aliphatic dicarboxaldehydes;

(c) feeding at least a portion of the polar phase from step (b) comprising water and the one or more aliphatic dicarboxaldehydes, with or without co-feeding additional water, into a hydrogenation zone, such that the total amount of water is equal to or greater than 10 weight percent, based on the weight of the total liquid feed to the hydrogenation zone, and hydrogenating the one or more aliphatic dicarboxaldehydes in a liquid phase with hydrogen in the presence of said water and in the presence of a hydrogenation catalyst under hydrogenation conditions sufficient to prepare one or more corresponding aliphatic diols.

DETAILED DESCRIPTION OF THE INVENTION

References herein to the Periodic Table of the Elements shall refer to the Periodic Table of the Elements published in *Nomenclature of Inorganic Chemistry: IUPAC Recommendations* 2005, Royal Society of Chemistry, 2005, ed. N. G. Connelly and T. Damhus. Also, any references to a Group or Groups of elements shall be to the Group or Groups reflected in this Periodic Table of the Elements using the IUPAC system for numbering groups.

"At least" is equivalent to "greater than or equal to," and "at most" is equivalent "to less than or equal to." All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageous" is used to denote a degree of preference more than required, but less than is denoted by the term "preferably."

Unless stated otherwise, when an element, material, or step capable of causing undesirable effects is present in amounts or in a form such that it does not cause the effect to an unacceptable degree, it is considered substantially absent for the practice of this invention. Furthermore, the terms "unacceptable" and "unacceptably" are used to refer to deviation from that which is considered commercially useful, otherwise useful in a given situation, or outside predetermined limits, which limits vary with specific situations and applications and are optionally set by predetermination, such as performance specifications. Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

In the description herein, several chemical terms are used that we define for purposes of this invention. When interpreting a meaning of a phrase, term, or word, its definition herein governs unless, for a particular use, a different meaning is stated elsewhere in this specification or unless a context of the use of the phrase, term, or word clearly indicates a different meaning is intended from the definitions provided herein.

Where a number of carbon atoms is appropriate to a particular chemical term (e.g., alkyl radical or group), the number is not set forth in the definition herein, because the number varies with each use of the chemical term. The later text sets forth a preferred number of carbon atoms for each use of the chemical term. The number of carbon atoms or a range thereof forming a moiety or compound is defined by prefixing the moiety or compound with a formula "$C_m$" or "$C_m\text{-}C_n$," respectively, wherein m and n are integers. For example, a $C_4$ alkane means the alkane has 4 carbon atoms, while a $C_1\text{-}C_{20}$ alkyl means the alkyl has a number of carbon atoms in the range from 1 to 20 carbon atoms.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises "a" ligand can be interpreted to mean that the ligand includes "one or more" ligands.

The term "comprising" is synonymous with "including," "containing," or "characterized by," is inclusive or open-ended, and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials, or steps are present, except that unrecited elements, materials or steps are optionally present to an extent that has no appreciable effect or are substantially absent.

The term "hydrocarbyl radical" or "hydrocarbon radical" refers to an organic radical comprised of carbon and hydrogen atoms, including linear, branched, cyclic, saturated, and unsaturated species, for example, alkyl, alicyclic, alkenyl, aryl, alkaryl, and aralkyl groups. The term "substituted hydrocarbyl" or "substituted hydrocarbon radical" refers to a hydrocarbyl or hydrocarbon radical that is substituted with one or more substituents as disclosed hereinafter. The hydrocarbyl or hydrocarbon radical can be univalent, divalent, or trivalent as specified in the text.

The term "aliphatic" refers to an organic compound or radical characterized by a straight chain or branched chain structure, or closed ring structure, any of which contains saturated carbon bonds, and optionally, one or more unconjugated carbon-carbon unsaturated bonds, such as a carbon-carbon double bond. For the purposes of this invention, the term "aliphatic" also includes "alicyclic" compounds defined hereinafter.

The term "alicyclic" refers to an aliphatic organic compound or radical containing a closed ring structure comprising saturated carbon bonds and, optionally, one or more unconjugated carbon-carbon double bonds.

The term "alkyl" refers to a saturated monovalent hydrocarbyl radical, which may be linear or branched, for example, methyl, ethyl, propyl, and isopropyl.

The term "alkylene" refers to a divalent alkyl radical.

The term "alkenyl" refers to a monovalent straight or branched chain hydrocarbyl radical containing one or more unconjugated unsaturated carbon-carbon double bonds.

The term "aryl" is defined as a univalent moiety derived from an arene by removal of one hydrogen atom from one carbon atom. The arene can contain a single aromatic ring or multiple aromatic rings that are fused together, directly linked, or indirectly linked (such that the different aromatic groups are bound to a common group such as a methylene or ethylene moiety). Preferred aryl groups contain one aromatic ring, or 2 to 4 fused or linked aromatic rings, for example, phenyl, naphthyl, biphenyl, and the like. The term "substituted aryl" refers to an aromatic group substituted with one or more substituents as noted hereinafter. As distinct from aliphatic compounds or alkyl or alkenyl radicals, an aryl radical contains conjugated carbon-carbon double bonds characterized by $(4\delta+2)$ $\pi$-electrons, where $\delta$ is an integer greater than or equal to 1.

The term "alkaryl" refers to a monovalent aryl radical with one or more alkyl substituents.

The term "arylalkyl" or "aralkyl" refers to a monovalent alkyl radical containing one aryl substituent.

As used herein, any and all of the terms "hydrocarbyl," "aliphatic," "alicyclic," "alkyl," "alkylene," "alkenyl," "aryl," "alkaryl," and "aralkyl" are intended to include substituted variants thereof. The term "substituted" or the words "substituted variants thereof" refer to the replacement of at least one hydrogen atom that is bonded to a carbon atom, for example, an alkyl or aryl carbon atom, with a non-hydrogen moiety. Preferred substituents for this invention include hydroxy, alkyl, aryl, aralkyl, and alkaryl radicals, wherein the aforementioned organic radicals contain from 1 to about 8 carbon atoms at most.

The term "optional" or "optionally" means that the subsequently described circumstance may or may not occur. For example, the term "optionally substituted" means that a non-hydrogen substituent may or may not be present on a given atom, and thus, the description includes structures wherein a non-hydrogen substituent is present and structures wherein a non-hydrogen substituent is not present.

As used herein, the phrase "having the formula" or "represented by the formula" is not intended to be limiting and is used in the same manner as the term "comprising" is commonly used.

The relevant teachings of each reference cited herein are incorporated to the maximum extent allowed by United States law.

As noted hereinabove, this invention in a fundamental aspect provides for hydrogenation of an aliphatic dialdehyde, preferably, a $C_6\text{-}C_{16}$ aliphatic dialdehyde, to form an aliphatic diol, preferably, a $C_6\text{-}C_{16}$ aliphatic diol. Said process comprises contacting one or more aliphatic dialdehydes in a liquid phase with hydrogen in the presence of a hydrogenation catalyst in a hydrogenation zone, and in the presence of water in an amount equal to or greater than 10 weight percent, based on the weight of the total liquid feed to the hydrogenation process. Moreover, the contacting is conducted under reaction conditions sufficient to prepare the one or more corresponding aliphatic diols.

In another aspect, this invention provides for the production of one or more aliphatic diols, preferably, one or more $C_6\text{-}C_{16}$ aliphatic diols, comprising:

(a) contacting in a hydroformylation zone an olefinically-unsaturated aliphatic aldehyde with carbon monoxide and hydrogen in the presence of a transition metal-organophosphorus ligand complex catalyst and, optionally, free organophosphorus ligand under hydroformylation conditions sufficient to prepare a hydroformylation product composition comprising one or more aliphatic dicarboxaldehydes, the transition metal-organophosphorus ligand complex catalyst, and optionally, free organophosphorus ligand;

(b) mixing in an extraction zone the hydroformylation product composition with water and, optionally, a nonpolar solvent under conditions sufficient to obtain by phase separation a nonpolar phase comprising the transition metal-organophosphorus ligand complex catalyst, optionally, free organophosphorus ligand, and optionally, the nonpolar solvent and a polar phase comprising water and the one or more aliphatic dicarboxaldehydes;

(c) feeding at least a portion of the polar phase from step (b) comprising water and the one or more aliphatic dicarboxaldehydes, with or without co-feeding additional water, into a hydrogenation zone, such that the total amount of water is equal to or greater than 10 weight percent, based on the weight of the total liquid feed to the hydrogenation zone, and hydrogenating the one or more aliphatic dicarboxaldehydes in a liquid phase with hydrogen in the presence of said water and in the presence of a hydrogenation catalyst under hydrogenation conditions sufficient to prepare one or more corresponding aliphatic diols.

In a preferred embodiment of this invention, the aliphatic dialdehyde comprises an alicyclic dialdehyde, more preferably, a monocyclic $C_6$-$C_{16}$ aliphatic dicarboxaldehyde, most preferably, a mixture of cis/trans-(1,3)(1,4)-cyclohexane dicarboxaldehydes. In a related preferred embodiment, the aliphatic diol comprises an alicyclic diol, more preferably, a monocyclic $C_6$-$C_{16}$ aliphatic diol, most preferably, a mixture of cis/trans-(1,3)(1,4)-cyclohexanedimethanol.

In another preferred embodiment of this invention, in the extraction stage of step (b), water is employed in an amount greater than about 4 weight percent, preferably, greater than about 10 weight percent, more preferably, greater than about 20 weight percent up to about 95 weight percent, based on the weight of the total feed to the extraction step. As used herein, the phrase "total feed to the extraction step" refers to the total liquid feed fed to an extractor in step (b), including but not limited to total water feed and/or co-feed, any other solvent(s) or diluent(s) as may be used including non-polar solvents and polar non-aqueous solvents, the one or more aliphatic dicarboxaldehydes, and any impurities and/or by-products present in the aliphatic dicarboxaldehyde(s) including but not limited to organophosphorus ligands, organophosphorus ligand degradation products, hemiacetals, acetals, lactones, and/or other heavies including dimers, trimers, and higher oligomers.

The aliphatic dialdehyde employed in the hydrogenation process of this invention comprises any aliphatic compound containing at least two carboxaldehyde (formyl) substituents (—CH=O). As noted hereinbefore, the term "aliphatic" refers to a hydrocarbon of straight chain, branched chain, or closed ring structure, wherein the carbon atoms (exclusive of formyl substituents) have fully saturated bonds, wherein each carbon atom is bonded to four other atoms in single bonds, as in an alkane, and optionally having one or more isolated (i.e., unconjugated) carbon-carbon double bonds, as in an olefin, such that the arrangement of any C=C double bonds does not classify as "aromatic." The preferred aliphatic dialdehyde comprises an alicyclic dialdehyde, which refers to an aliphatic closed ring system of one or more rings, fused or linked, saturated or unsaturated, but without aromaticity, and further comprises two carboxaldehyde substituents, either directly attached to a ring carbon or attached to a substituent that is attached to a ring carbon. A more preferred aliphatic dialdehyde comprises a monocyclic $C_6$-$C_{16}$ aliphatic dicarboxaldehyde comprising a single aliphatic ring compound having a total of 6 to 16 carbon atoms including two carboxaldehyde substituents and any other carbon-containing substituents. Preferably, the monocyclic $C_6$-$C_{16}$ aliphatic dicarboxaldehyde is represented by the following formula (I):

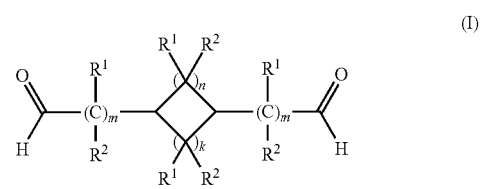

wherein each $R^1$ is independently selected from hydrogen, hydroxy, and $C_1$-$C_6$ monovalent hydrocarbyl radicals, preferably, hydrogen and $C_1$-$C_3$ alkyl radicals; wherein each $R^2$ is independently selected from hydrogen, hydroxy, and $C_1$-$C_6$ monovalent hydrocarbyl radicals, preferably, hydrogen and $C_1$-$C_3$ alkyl radicals; each n is an integer from 0 to about 6, preferably, from 0 to 3, more preferably, 2; each k is an integer from 0 to about 6, preferably, from 0 to 3, more preferably, 2; n+k is greater than 2; and each m is independently an integer from 0 to about 3, preferably, 0 or 1. It is noted that if n or k is 0, then the two chains containing m carbon atoms are directly linked to each other. $R^1$ and $R^2$ can be substituted with one or more substantially inert substituents that do not interfere with the process of this invention, non-limiting examples of which include hydroxy, alkyl, aryl, aralkyl, and alkaryl radicals, wherein the aforementioned organic radicals preferably comprise from 1 to about 8 carbon atoms. Preferably, the inert substituent comprises hydroxy. Any selections within the definitions of $R^1$, $R^2$, n, m, k are acceptable, provided that the total number of carbon atoms in the dicarboxaldehyde does not exceed an upper limit of 16.

Non-limiting examples of suitable monovalent aliphatic $C_6$-$C_{16}$ dicarboxaldehydes for use in the hydrogenation process of this invention include cis-1,3-cyclohexane dicarboxaldehyde, trans-1,3-cyclohexane dicarboxaldehyde, cis-1,4-cyclohexane dicarboxaldehyde, trans-1,4-cyclohexane dicarboxaldehyde, cis-1,3-cyclooctane dicarboxaldehyde, trans-1,3-cyclooctane dicarboxaldehyde, cis-1,4-cyclooctane dicarboxaldehyde, trans-1,4-cyclooctane dicarboxaldehyde, cis-1,5-cyclooctane dicarboxaldehyde, and trans-1,5-cyclooctane dicarboxaldehyde, mixtures of any of the aforementioned compounds, and analogues thereof. Most preferably, the monocyclic $C_6$-$C_{16}$ aliphatic dicarboxaldehyde comprises a mixture of cis and trans-1,3- and 1,4-cyclohexane dicarboxaldehydes ("cis/trans-(1,3)(1,4)-cyclohexanedicarboxaldehyde). Two of the possible four isomers of said cyclohexanedicarboxaldehyde are represented by the following Formulas IIa (1,3-isomer in trans form, but can also exist as a cis isomer) and IIb (1,4-isomer in cis form, but can also exist as a trans isomer):

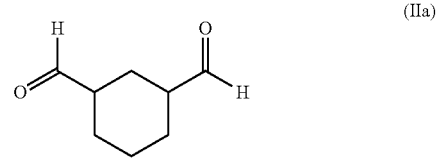

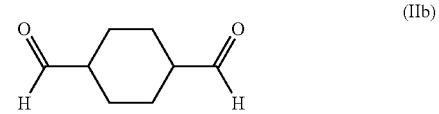

Advantageously, the more preferred isomeric mixture of cis/trans-(1,3)(1,4)-cyclohexanedicarboxaldehyde comprises from about 50 to 60 percent 1,3-isomer and from about 40 to 50 percent 1,4-isomer, by weight.

The aliphatic dicarboxaldehyde can contain small quantities of impurities and byproducts resulting from the hydroformylation process from whence the aliphatic dicarboxaldehyde is preferentially produced. Impurity carboxylic acids, characterized by one or two RC(O)OH functionalities, where R represents a monovalent hydrocarbyl radical, may arise from oxidation of the mono-carboxaldehyde reactant and di-carboxaldehyde product of the hydroformylation process. Hemiacetals can arise from hydrolysis of aldehyde products during hydroformylation or simple condensation of an alcohol with an aldehyde during subsequent hydrogenation. Hemiacetals are advantageously characterized as hydrated aldehydes, $RHC(OH)_2$ or $RHC(OR')(OH)$, where R and R' represent monovalent hydrocarbyl radicals which can be the same or different. Organophosphites and degradation products from organophosphites can be present as impurities, the likely source being the ligands used in the hydroformylation catalysts. Other impurities include heavies, such as dimers, trimers, and higher oligomers formed during hydroformylation or the subsequent hydrogenation. As used herein, the term "heavies" more particularly refers to compounds that have a molecular weight higher than that of the dicarboxaldehyde or a normal boiling point higher than that of the diol. Referring to the diol, the term "normal boiling point" is defined herein as the temperature at which the liquid and gaseous phases of the diol exist in equilibrium at a diol vapor pressure of 1 atmosphere (101 kPa). Typically, the aforementioned aliphatic dialdehydes employed in the hydrogenation process of this invention comprise at the start from about 0.005 to about 5 weight percent each of acetals, hemiacetals, and other heavies (including dimers, trimers and higher oligomers), calculated on the total weight of the aliphatic dialdehyde.

The identification of the aliphatic dialdehyde and accompanying impurities is conventional and includes various well known analytical methods including, but not limited to, gas phase chromatography (GC) optionally coupled with mass spectrometry analyzers (GC-MS), gel permeation chromatography (GPC), $^1H$, $^{13}C$, and $^{31}P$ nuclear magnetic resonance spectroscopy, and infrared spectroscopy.

The aliphatic dialdehydes can be prepared by synthetic methods known to those of skill in the art, as disclosed for example in U.S. Pat. No. 6,252,121B1 and U.S. Pat. No. 6,307,110B1 and U.S. Pat. No. 5,952,530, incorporated herein by reference. Preferably, the monocyclic $C_6$-$C_{16}$ aliphatic dicarboxaldehyde is prepared via hydroformylation of an alicyclic olefinically-unsaturated carboxaldehyde described, for example, in U.S. Pat. No. 6,252,121B1, which in particular discloses contacting an alicyclic olefinically unsaturated carboxaldehyde with carbon monoxide and hydrogen (synthesis gas or syngas) in the presence of a transition metal-organophosphorus ligand complex catalyst under reaction conditions sufficient to convert the olefinic group into a carboxaldehyde group thereby forming an alicyclic dicarboxaldehyde product. The alicyclic olefinically-unsaturated carboxaldehyde is suitably prepared in a Diels Alder addition of a diene, that is, a compound having a conjugated pair of olefinically-unsaturated carbon-carbon double bonds, with a dienophile, that is, a compound favorably inclined to react with a diene, such as, an olefinically-unsaturated carboxaldehyde. In a most preferred example, butadiene is reacted with acrolein in a Diels Alder addition to produce 1,2,3,6-tetrahydrobenzaldehyde as an alicyclic olefinically-unsaturated carboxaldehyde, which is hydroformylated with syngas in the presence of a rhodium-triorganophosphite ligand complex catalyst to prepare cis/trans-(1,3)(1,4)-cyclohexanedicarboxaldehyde.

Illustrative olefinically-unsaturated dienes that can be suitably converted via the aforementioned Diels Alder condensation into olefinically-unsaturated carboxaldehydes include without limitation butadiene, isoprene, and 1,3-cyclooctadiene. Examples of the resulting cyclic unsaturated aldehydes include: 3- or 4-dicarboxycyclohexane (butadiene+acrolein), and 3- or 4-cyano-formylcyclohexane (butadiene+acrylonitrile). Other dienes that can be hydroformylated into dicarboxaldehydes include but are not limited to 1,4-cycloheptadiene, 4-vinylcyclohexene (butadiene dimer), 1,4-cyclooctadiene, and 1,5-cyclooctadiene.

Metal-organophosphorus ligand complex catalysts employable in the hydroformylation process to prepare the aliphatic dicarboxaldehyde are well known in the art and include those disclosed in the above-mentioned referenced patents. In general, such catalysts can be preformed or formed in situ in the hydroformylation process, and consist essentially of metal in complex combination with an organophosphorus ligand, preferably, an organophosphite ligand. It is believed that carbon monoxide is also present and complexed with the metal in the active species, which also can contain hydrogen directly bonded to the metal.

The permissible metals that make up the metal-ligand complex include the transition metals from Groups 8, 9 and 10 of the Periodic Table, selected from rhodium (Rh), cobalt (Co), iridium (Ir), ruthenium (Ru), iron (Fe), nickel (Ni), palladium (Pd), platinum (Pt), osmium (Os), and mixtures thereof, with the preferred metals being rhodium, cobalt, iridium and ruthenium, more preferably rhodium, cobalt and ruthenium, and most preferably, rhodium. Other permissible metals include Group 6 metals selected from chromium (Cr), molybdenum (Mo), tungsten (W), and mixtures thereof. Mixtures of metals from Groups 6, 8, 9 and 10 can also be used in this invention. The number of available coordination sites on such metals is well known in the art. Thus the hydroformylation catalyst can comprise a complex catalyst mixture in monomeric, dimeric or higher nuclearity forms that are preferably characterized by at least one organophosphorus-containing molecule complexed per one molecule of metal, for example, rhodium.

The term "complex" as used herein and in the claims means a coordination compound formed by the union of one or more electronically rich molecules or atoms with one or more electronically poor molecules or atoms. For example, the organophosphite ligands employable herein possess one or more phosphorus donor atoms, each having one available or unshared pair of electrons, which each is capable of forming a coordinate covalent bond independently or possibly in concert (for example, via chelation) with the metal. Carbon monoxide can also be present and complexed with the metal. The ultimate composition of the complex catalyst can also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted monovalent hydrocarbon radical, for example, alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefins, diolefins and triolefins, tetrahydrofuran, and the like.

Preferred organophosphorus ligands that make up the metal-organophosphorus ligand complex and free organophosphorus ligand include organomonophosphites and organopolyphosphites. Mixtures of such ligands can be employed if desired in the metal-organophosphite ligand complex catalyst and/or free ligand, and such mixtures of free and complexed ligands can be the same or different.

Representative monoorganophosphites include those having Formula III:

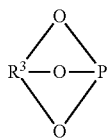

(III)

wherein $R^3$ represents a substituted or unsubstituted trivalent hydrocarbon radical containing from about 4 to 40 carbon atoms, such as trivalent acyclic and trivalent cyclic radicals, e.g., trivalent alkylene radicals such as those derived from 1,2,2-trimethylolpropane, or trivalent cycloalkylene radicals, such as those derived from 1,3,5-trihydroxycyclohexane. Such monoorganophosphites can be found described in greater detail, for example, in U.S. Pat. No. 4,567,306, the disclosure of which is incorporated herein by reference.

Representative diorganophosphites include those having Formula IV:

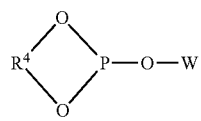

(IV)

wherein $R^4$ represents a substituted or unsubstituted divalent hydrocarbon radical containing from about 4 to 40 carbon atoms and W represents a substituted or unsubstituted monovalent hydrocarbon radical containing from 1 to about 18 carbon atoms.

Representative substituted and unsubstituted monovalent hydrocarbon radicals represented by W in the above formula include alkyl and aryl radicals, while representative substituted and unsubstituted divalent hydrocarbon radicals represented by $R^4$ include divalent acyclic radicals and divalent aromatic radicals. Illustrative divalent acyclic radicals include, for example, alkylene, alkylene-oxy-alkylene, alkylene-NX-alkylene, wherein X is hydrogen or a substituted or unsubstituted monovalent hydrocarbon radical, alkylene-S-alkylene, and cycloalkylene radicals. The more preferred divalent acyclic radicals are the divalent alkylene radicals, such as disclosed more fully, for example, in U.S. Pat. No. 3,415,906, U.S. Pat. No. 4,567,306, the disclosures of which are incorporated herein by reference. Illustrative divalent aromatic radicals include, for example, arylene bisarylene, arylene-alkylene, arylene-alkylene-arylene, arylene-oxy-arylene, arylene-NX-arylene, wherein X is as defined above, arylene-S-arylene, and arylene-S-alkylene. More preferably, $R^4$ is a divalent aromatic radical, such as disclosed more fully, for example, in U.S. Pat. No. 4,599,206 and U.S. Pat. No. 4,717,775, the disclosures of which are incorporated herein by reference.

Representative of a more preferred class of diorganophosphites are those of Formula V:

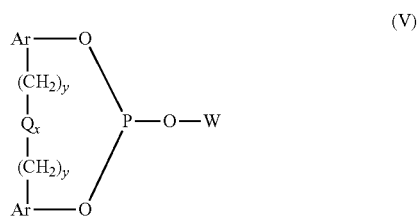

(V)

wherein W is as defined above, each Ar is the same or different and represents a substituted or unsubstituted divalent aryl radical, each y is the same or different and is a value of 0 or 1, Q represents a divalent bridging group selected from —C($R^5$)$_2$—, —O—, —S—, —N$R^6$—, —Si($R^7$)$_2$— and —CO, wherein each $R^5$ is the same or different and is selected from hydrogen, alkyl radicals having from 1 to 12 carbon atoms, phenyl, tolyl, and anisyl, $R^6$ represents hydrogen or an alkyl radical of from 1 to 10 carbon atoms, preferably, methyl, each $R^7$ is the same or different and represents hydrogen or an alkyl radical having from 1 to about 10 carbon atoms, preferably, methyl, and x is a value of 0 or 1. Such diorganophosphites are described in greater detail, for example, in U.S. Pat. No. 4,599,206, U.S. Pat. No. 4,717,775, and U.S. Pat. No. 4,835,299, the disclosures of which are incorporated herein by reference.

Representative triorganophosphites can include those having Formula VI:

(VI)

wherein each $R^8$ is the same or different and is a substituted or unsubstituted monovalent hydrocarbon radical, for example, an alkyl, cycloalkyl, aryl, alkaryl, or aralkyl radical, which can contain from 1 to 24 carbon atoms. Illustrative triorganophosphites include, for example, trialkylphosphites, dialkylarylphosphites, alkyldiarylphosphites, and triarylphosphites, such as, triphenylphosphite, tris(2,6-triisopropyl) phosphite, tris(2,6-di-tert-butyl-4-methoxyphenyl) phosphite, as well as the more preferred tris(2,4-di-tert-butylphenyl) phosphite. The monovalent hydrocarbon radical moieties themselves can be functionalized with the proviso that said functional groups do not significantly interact with the transition metal or otherwise inhibit hydroformylation. Representative functional groups include alkyl or aryl radicals, ethers, nitriles, amides, esters, —N($R^6$)$_2$, —Si($R^7$)$_3$, phosphates, and the like, wherein $R^6$ and $R^7$ are defined hereinbefore. Such triorganophosphites are described in more detail in U.S. Pat. No. 3,527,809, the disclosures of which are incorporated herein by reference.

Any of the groups $R^3$ to $R^8$ can be substituted with one or more inert substituents. More specifically, illustrative substituents include, for example, primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, and octadecyl; aryl radicals such as phenyl and naphthyl; aralkyl radicals such as benzyl, phenylethyl, and triphenylmethyl; alkaryl radicals such as tolyl and xylyl; alicyclic radicals such as cyclopentyl, cyclohexyl, 1-methylcyclohexyl, cyclooctyl, and cyclohexylethyl; alkoxy radicals such as methoxy, ethoxy, propoxy, t-butoxy, —OCH₂CH₂OCH₃, —O(CH₂CH₂)₂OCH₃, and —O(CH₂CH₂)₃OCH₃; aryloxy radicals such as phenoxy; as well as silyl radicals such as —Si(CH₃)₃, —Si(OCH₃)₃, and —Si(C₃H₇)₃; amino radicals such as —NH₂, —N(CH₃)₂, —NHCH₃, and —NH(C₂H₅); arylphosphine radicals such as —P(C₆H₅)₂; acyl radicals such as —C(O)CH₃, —C(O)C₂H₅, and —C(O)C₆H₅; carbonyloxy radicals such as —C(O)OCH₃; oxycarbonyl radicals such as —O(CO)C₆H₅; amido radicals such as —CONH₂, —CON(CH₃)₂, and —NHC(O)CH₃; sulfonyl radicals such as —S(O)₂C₂H₅; sulfinyl radicals such as —S(O)CH₃; sulfenyl radicals such as —SCH₃, —SC₂H₅, and —SC₆H₅; phosphonyl radicals such as —P(O)(C₆H₅)₂, —P(O)(CH₃)₂, —P(O)(C₂H₅)₂, —P(O)(C₃H₇)₂, —P(O)(C₄H₉)₂, —P(O)(C₆H₁₃)₂, —P(O)CH₃(C₆H₅), and —P(O)(H)(C₆H₅).

A most preferred organophosphorus ligand comprises a triorgano-monophosphite ligand, more preferably, tris-(2,4-di-tert-butylphenyl)phosphite represented by Formula VII:

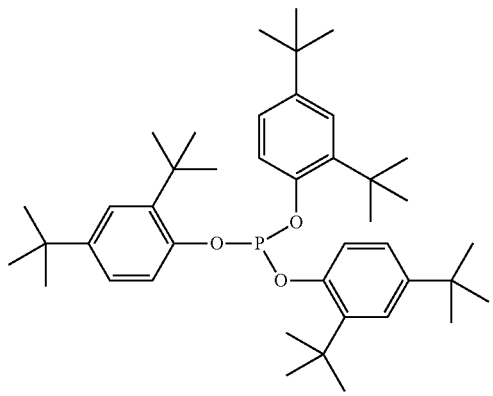

(VII)

The amount of metal-ligand complex catalyst present in the reaction fluid of the hydroformylation process to prepare the aliphatic dialdehyde need only be that minimum amount necessary to catalyze the selected hydroformylation. Metal, preferably, rhodium, concentrations in the range of from about 10 parts per million to about 1000 parts per million, calculated as free metal in the hydroformylation reaction fluid are advantageously employed for most processes, while it is preferred to employ from about 10 to 500 parts per million of metal, and more preferably from 25 to 350 parts per million of metal.

In addition to the metal-ligand complex catalyst, free ligand (that is, ligand not complexed with the metal) can also be present in the hydroformylation reaction fluid, if desired. The free ligand can correspond to any of the aforementioned organophosphorus ligands. Advantageously, from about 0.1 mole to about 100 moles of free ligand per mole of metal in the hydroformylation reaction fluid are employed. Preferably the hydroformylation process is carried out in the presence of from about 1 to about 50 moles of ligand, and more preferably from about 1.1 to about 4 moles of ligand, per mole of metal present in the reaction fluid; said amounts of ligand being the sum of both the amount of ligand that is bound (complexed) to the metal and the amount of free (non-complexed) ligand present. If desired, make-up or additional ligand can be supplied to the reaction fluid of the hydroformylation process at any time and in any suitable manner to maintain a predetermined level of free ligand in the reaction fluid.

The reaction conditions of the hydroformylation process to prepare the aliphatic dicarboxaldehyde are sufficiently disclosed in the art. For example, the H₂:CO molar ratio of gaseous hydrogen to carbon monoxide advantageously ranges from about 1:10 to 100:1, the more preferred molar ratio being from about 1:10 to about 10:1. Advantageously, the hydroformylation is conducted at a reaction temperature greater than about −25° C., more preferably, greater than about 50° C., but less than about 200° C., and preferably, less than about 120° C. Advantageously, the total gas pressure comprising hydrogen, carbon monoxide and olefinic reactant ranges from about 1 psia (6.8 kPa) to about 10,000 psia (68.9 MPa), preferably, from about 1 psia (6.8 kPa) to less than about 2,000 psia (13,800 kPa), and more preferably, from about 1 psia (6.8 kPa) to less than about 500 psia (3,450 kPa). The carbon monoxide partial pressure advantageously ranges from about 1 psia (6.8 kPa) to about 1000 psia (6,900 kPa), and preferably, from about 3 psia (20.7 kPa) to about 800 psia (5,516 kPa); while the hydrogen partial pressure advantageously ranges from about 5 psia (34.5 kPa) to about 500 psia (3,450 kPa), and preferably, from about 10 psia (68.0 kPa) to about 300 psia (2,070 kPa). Feed flow rates are known in the art as described, for example, in "Process Economics Program Report 21D: Oxo Alcohols 21d," SRI Consulting, Menlo Park, Calif., Published December 1999, incorporated herein by reference.

The hydroformylation product composition obtained from the hydroformylation step comprising one or more aliphatic dialdehydes, the transition metal-organophosphorus ligand complex catalyst, and optional free organophosphorus ligand is thereafter subjected to phase separation to separate the one or more aliphatic dialdehyde products and to recover a recycle stream containing the transition metal-organophosphorus ligand complex catalyst and optional free organophosphorus ligand for recycle to the hydroformylation process. Of course, the hydroformylation product composition can contain additional components including, for example, unconverted olefinically-unsaturated carboxaldehyde reactant, hydrocarbon solvent(s) as may have been used, saturated aliphatic carboxaldehyde arising from hydrogenation of the olefinically-unsaturated carboxaldehyde, and potentially also, olefinic isomers of the olefinically-unsaturated carboxaldehyde reactant, as well as heavies and other impurities mentioned hereinbefore.

Except where noted hereinafter, the extraction step is suitably described in the art, for example, in U.S. Pat. No. 6,252,121B1, incorporated herein by reference. In the extraction, the hydroformylation product composition comprising one or more aliphatic dialdehydes, preferably, one or more alicyclic dicarboxaldehydes, the transition metal-organophosphorus ligand complex catalyst, and optional free organophosphorus ligand is mixed with water and optionally a nonpolar solvent under conditions sufficient to obtain by phase separation a nonpolar phase comprising the transition metal-organophosphorus ligand complex catalyst, optionally, the free organophosphorus ligand, and optionally, the nonpolar solvent and a polar phase comprising water and one or more aliphatic dialdehyde products.

Water is the preferred extraction solvent. Optionally, one or more non-aqueous polar solvents can be employed with water. Non-limiting examples of suitable non-aqueous polar solvents include C₁-C₆ alkanols, such as methanol, ethanol, propanol, butanol, higher homologues thereof, and mixtures of the foregoing compounds. The total quantity of water and non-aqueous polar solvent(s) should be sufficient to induce phase separation of the hydroformylation product composition. More preferably, the total quantity of water and non-aqueous polar solvent(s) is sufficient not only to induce phase separation of the hydroformylation product composition, but to substantially extract more than about 85 weight percent, and preferably, more than about 90 weight percent of the aliphatic dicarboxaldehyde product(s) into one polar aqueous layer or phase.

Preferably, any one of two methods is used to implement the extraction step. In one preferred embodiment, the quantity of water and non-aqueous polar solvent(s) employed in the extraction comprises greater than about 10 percent up to about 20 percent, by weight, based on the weight of the total feed to the extractor. In this embodiment, the water level exceeds the preferred range disclosed in the prior art and results advantageously in three liquid layers or phases: a non-polar phase comprising the non-polar solvent (if any), hydroformylation catalyst, and free organophosphorus ligand; an aqueous phase comprising water and any polar non-aqueous solvent; and an organic polar phase comprising the aliphatic dicarboxaldehyde. In another preferred embodiment, the quantity of water and non-aqueous polar solvent(s) employed in the extraction comprises greater than about 20 percent, more preferably, greater than about 50 percent, up to about 95 percent, based on the weight of the total feed to the extraction step. More preferably, in this embodiment, the water level exceeds 50 percent and most preferably ranges between about 80 and 95 percent, by weight, based on the weight of the total feed to the extractor. In this latter embodiment, the water is well-beyond the range disclosed in the prior art and results advantageously in two, rather than three, phases: a non-polar phase comprising the non-polar solvent (if any), hydroformylation catalyst, and free organophosphorus ligand and a polar phase comprising water, any polar non-aqueous solvent(s), and the one or more aliphatic dicarboxaldehydes essentially completely dissolved therein such that the polar phase comprises only one layer.

Depending upon the particular hydroformylation catalyst and reactants employed, one or more nonpolar solvents can be employed in the extraction step, if desired, such as liquid alkanes, cycloalkanes, alkenes, aromatic hydrocarbons, and mixtures thereof. Illustrative nonpolar solvents include, without limitation, 2,2-dimethylpropane, 2,2-dimethylbutane, pentane, isopropyl ether, hexane, heptane, octane, nonane, decane, isobutyl isobutyrate, tributyl heptyl ketone, diisobutyl ketone, cyclopentane, cyclohexane, isobutylbenzene, n-nonylbenzene, n-octylbenzene, p-xylene, ethylbenzene, 1,3,5-trimethylbenzene, m-xylene, toluene, o-xylene, decene, dodecene, and tetradecane. U.S. Pat. No. 6,252,121 and U.S. Pat. No. 6,307,110, incorporated herein by reference, describe additional usable nonpolar solvents. If used, the amount of nonpolar solvent is not critical and advantageously ranges from about 1 percent up to about 20 percent, by weight, based on the total weight of the hydroformylation product composition fed to the extractor.

Advantageously, a portion or all of the hydroformylation product composition is withdrawn from the hydroformylation zone and fed to an extractor, wherein water and, optionally, other polar and nonpolar solvents are also fed; and the total mixture is mixed and allowed to settle, or alternatively, the components are fed to a decanter and allowed to settle into two or three phases as noted hereinbefore.

From the extractor or decanter, the phase containing the aliphatic dicarboxaldehyde is fed in whole or in part, as desired, to the hydrogenation zone. At this point, the quantity of water fed to the hydrogenation zone can be adjusted to ensure a quantity equal to or greater than 10 weight percent, preferably greater than 10 weight percent, and more preferably, greater than about 15 weight percent, and even more preferably greater than about 20 weight percent, based on the weight of the total liquid feed to the hydrogenation. A preferred quantity of water is less than about 95 weight percent. An even more preferred quantity of water is equal to or greater than about 20 and less than about 95 weight percent, based on the weight of the total liquid feed to the hydrogenation. Thus, if the aliphatic dicarboxaldehyde-containing phase from the extractor or decanter contains too little water, it will be necessary to co-feed additional water into the hydrogenation zone to increase the water level to that required for the hydrogenation. On the other hand, if the quantity of water in the aqueous polar phase from the extractor or decanter is too high, it may be necessary to remove water from the polar phase via e.g., distillation or evaporation, to reduce the water level to that required for the hydrogenation. Preferably, the water level needs no adjustment or needs to be increased through a simple co-feed of additional water.

When the water fed to the hydrogenation is equal to or greater than about 20 weight percent, as noted hereinabove, then the quantity of water employed in the hydrogenation is preferably greater than about 4 mole equivalents of water per mole equivalent of aliphatic dicarboxaldehyde or greater than about 2 mole equivalents of water per mole equivalent formyl substituent fed to the hydrogenation zone.

In the process of this invention, the hydrogenation of the aliphatic dialdehydes is conducted in a liquid phase, preferably, in continuous or intermittent flow contact with a hydrogenation catalyst. The catalyst is provided to the hydrogenation zone usually in a solid fixed bed, preferably, as precipitated, pelletized, shaped, or extruded particles. Other types of hydrogenation reactors or zones are also feasible including batch reactors, fluidized bed reactors, trickle bed reactors, single and multiple pass reactors as known to the skilled person. The reaction can be conducted adiabatically or isothermally, in one or more stages as desired. Unconverted aliphatic dialdehyde can be recycled back to the hydrogenation reactor for further conversion. A portion of the aliphatic diol product can be recycled to the hydrogenation zone to be used as a diluent, if desired.

The hydrogenation catalyst comprises one or more metals selected from Groups 6, 7, 8, 9, 10, 11, and 12 of the Periodic Table, preferably, Groups 6, 10, and 11, more preferably, chromium, nickel, copper, palladium, platinum, and mixtures thereof. It is possible to employ the catalytic metal in a carrier-free form or alternatively affixed to a carrier or support, such as aluminum oxide, silicon oxide, titanium oxide, an aluminosilicate, carbon, and any other conventional support material known to the skilled person. If a carrier or support is employed, the loading of the total catalytic metal(s) onto the carrier or support advantageously ranges from about 0.01 weight percent up to about 20 weight percent, although other loadings of a lesser or greater amount can be employed. The hydrogenation catalyst optionally can comprise additional materials and/or stabilizers that promote and/or stabilize the hydrogenation reaction to the desired aliphatic diols. Such additional materials and/or stabilizers include, without limit, alkali metal and alkaline earth metal oxides and alkali metal and alkaline earth metal hydroxides. Carrier materials, such as silica and alumina, can be added to the catalyst to improve the physical properties thereof, for example, attrition resistance. A preferred catalyst comprises nickel supported on alumina. A preferred catalyst excludes sulfactive hydrogenation catalysts, such as, Group 6, 7, 8, 9, 10, 11, and 12 sulfides, preferably, molybdenum sulfide, tungsten sulfide, and nickel sulfide.

The hydrogenation process conditions can vary depending upon the particular species of aliphatic dialdehyde and catalyst employed. Advantageously, hydrogen is introduced in an excess amount relative to total carbonyl (formyl) groups in the aliphatic dialdehyde feed. Preferably, the molar ratio of hydrogen to moles of carbonyl (formyl) groups is greater than 1.3:1, more preferably, greater than about 1.5:1. Preferably, the molar ratio of hydrogen to moles of carbonyl groups is less than about 10:1, and more preferably less than about 5:1, and even more preferably, less than about 3:1.

The hydrogenation advantageously is conducted at a temperature greater than about 40° C., preferably, greater than about 70° C., and advantageously conducted at a temperature less than about 200° C., preferably, less than about 150° C. The hydrogenation advantageously is conducted at a hydrogen pressure greater than about 3 bar (300 kPa), and preferably, greater than about 5 bar (500 kPa), and advantageously conducted at a hydrogen pressure less than about 50 bar (5,000 kPa), and preferably, less than about 30 bar (3,000 kPa). In a continuous mode of operation, the liquid hourly space velocity of the liquid aliphatic dialdehyde feed, containing at least some concentration of water carry-over from the extraction process, advantageously ranges from about 0.01 cm$^3$ liquid feed per cm$^3$ catalyst per hour (h$^{-1}$) to about 100 h$^{-1}$. The liquid hourly space velocity of any additional water feed is determined on the basis of the water content of the dialdehyde feed and the desired weight percentage of water in the total liquid feed to the hydrogenation.

A hydrogenation effluent stream is recovered from the hydrogenation reactor, from which one or more aliphatic diols can be separated and recovered by any convenient method known to the skilled person. Such separation methods include, for example, fractional distillation, extraction, crystallization, chromatography, and membrane filtration. A preferred method involves distillation as described in unpublished U.S. provisional patent application Ser. No. 60/962,548, filed Jul. 30, 2007, in the name of Glenn A Miller, Edward Yonemoto, and Ranier Potthast and entitled "PROCESS OF REFINING C$_6$-C$_{16}$ ALIPHATIC DIOLS," now pending as International Patent Application PCT/US2008/069308, filed Jul. 7, 2008. A first distillation is conducted advantageously at atmospheric pressure to remove lights, followed by a second distillation under reduced pressure to recover the desired diol product(s).

The preferred monocyclic C$_6$-C$_{16}$ aliphatic diol can be represented by the following Formula (VIII)

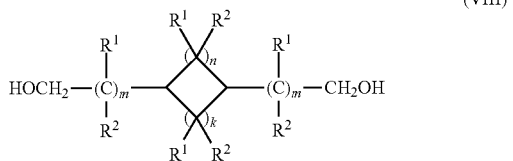

(VIII)

wherein each R$^1$ is independently selected from hydrogen, hydroxy, and C$_1$-C$_6$ monovalent hydrocarbyl radicals, preferably, hydrogen and C$_1$-C$_3$ alkyl radicals; each R$^2$ is independently selected from hydrogen, hydroxy, and C$_1$-C$_6$ hydrocarbyl radicals, preferably, hydrogen and C$_1$-C$_3$ alkyl radicals; n is an integer from 0 to about 6, preferably, from 0 to 3, more preferably, 2; k is an integer from 0 to about 6, preferably, from 0 to 3, more preferably, 2; n+k is greater than 2; and each m is independently an integer from 0 to about 3, preferably, 0 or 1. It is noted that if n or k is 0, then the two chains of m carbon atoms are directly linked. R$^1$ and R$^2$ can be substituted with one or more substantially inert substituents, as described hereinbefore. Preferably, the inert substituent comprises hydroxy. Again, R$^1$, R$^2$, m, n, and k can assume any of the defined values herein, provided that the total number of carbon atoms in the dialdehyde does not exceed 16.

The most preferred C$_6$-C$_{16}$ aliphatic diol comprises cis/trans-(1,3)(1,4)-cyclohexanedimethanol. Two of the four possible isomers are represented by Formulas IXa (1,3-isomer shown in trans form, but can also occur in cis form) and IXb (1,4-isomer shown in cis form, but can also occur in trans form):

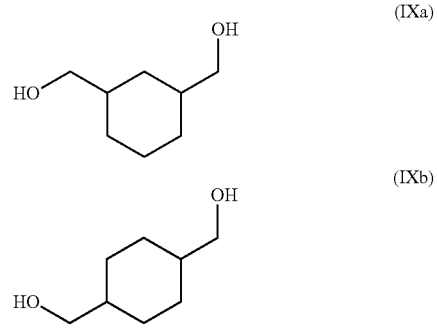

When the hydrogenation of the aliphatic dialdehyde is conducted in accordance with the invention, that is, in the presence of water in an amount equal to or greater than 10 weight percent, more preferably, greater than about 15 weight percent, and even more preferably greater than about 20 and less than about 95 weight percent, based on the weight of the total liquid feed to the hydrogenation zone, the yield of undesirable heavies is reduced, while the yield of the desired aliphatic diol is increased. The diol yield is increased from about 1.5 to about 2.0 weight percent, as compared to a similar process using water in an amount less than 10 weight percent.

The following examples are provided as illustrative of the invention; however, the examples are not intended to be limiting thereof. In view of the description herein, the skilled person will understand how to vary the examples within the scope of the claims.

Reactor Apparatus

A hydrogenation reactor is assembled consisting of a 106.7 cm (42 inch long), 3.5 cm (1.36 inch) inside diameter stainless steel pipe. The reactor is loaded with a nickel-alumina precipitate catalyst (50-60 wt % Ni, Engelhard, Catalog no. E3288), and a small plug of glass wool on each end to contain the catalyst. Pressure is controlled by a control valve with a pressure transducer on the outlet of the reactor. Temperature of the reactor is controlled with multiple heat tapes and several layers of insulation to distribute the heat uniformly.

A liquid dialdehyde feed is delivered via a feed pump. Gaseous hydrogen is controlled through a flow meter, and liquid and gas phases are mixed upstream in a pre-heater prior to entering the bottom of the upflow reactor. An alcohol product leaves the top of the reactor and is cooled by ambient exposure prior to sampling. Some of the product is recycled back to the feed stream as a diluent. The liquid product is collected and analyzed via a HP 6890 gas chromatograph (GC) equipped with a DB WAX (30 meter×0.32 mm×0.25 micron) capillary column. The sample is also analyzed by gel-permeation chromatography (GPC) which resolves diols from heavies, such as dimer and trimer species. Water in the feed and product is analyzed via Karl Fischer titration.

Example 1

A hydrogenation reactor configured as above is loaded with the aforementioned nickel-based catalyst (1000 cc). A dialdehyde feed, one of three independent co-feeds, is fed to the hydrogenation reactor, the dialdehyde feed comprising by weight: 4 percent water, 87 percent total dialdehyde isomers including cis and trans isomers of 1,3- and 1,4-cyclohexanedicarboxaldehyde, 7 percent heptane, and 2 percent others, including tetrahydrobenzaldehyde, cyclohexane carboxaldehyde, heavies, and acids. The effluent from the reactor is divided such that 10 weight percent is taken as product and 90 weight percent is recycled back to the hydrogenation reactor as diluent. Additional water is co-fed to the hydrogenation reactor. The total water-dialdehyde and recycle feeds are fed at a total liquid hourly space velocity (LHSV) of 1.0 hr$^{-1}$. Of the total flow, the dialdehyde feed is maintained at 10 weight percent; water is adjusted to 20 weight percent, with recycle from the hydrogenation reactor making up the remainder of the flow, the weight percentages being based on the weight of the total liquid feeds to the hydrogenation reactor. The 20 weight percent water is equivalent to 10 mole equivalents water per mole equivalent of dialdehyde or 5 moles water per mole formyl substituent. The combined feed provides for an acceptable viscosity for processing and handling. A preheater to the reactor is heated to 110° C. and the reactor itself is maintained between 100-140° C. The reactor is pressurized to 4826 kPa (700 psig) with hydrogen. The hydrogen is fed at 50 standard liters per hour or 50 percent molar excess required for full conversion to the diols. The catalyst bed temperature increases from 100° C. to 140° C. due to exothermic heat of reaction. The process is run for 2100 hours (87.5 days) with product sampling, approximately every 24 hours. Each product sample, comprising the desired cis/trans-(1,3)(1,4)-cyclohexane dimethanol, is evaluated by GC, GPC, and Karl Fischer titration, with the average results over the run summarized in Table 1.

TABLE 1

Analysis of Hydrogenation Product[a]

| Water in Feed | Heavies | | |
|---|---|---|---|
| To Hydrogenation (wt %)[b] | Hemiacetal (wt %) | Dimers (wt %) | Trimers (wt %) |
| CE-1    4 | 1.0 | 1.4 | 1.9 |
| Ex. 1   20 | 0.8 | 1.0 | 0.8 |

[a]Balance of hydrogenation product, exclusive of hemiacetal, dimers, and trimers, consists of a mixture of cis/trans-(1,3)(1,4)-cyclohexane dimethanol.
[b]Water feed to hydrogenation is given in weight percent, based on weight of total liquid feed to the hydrogenation.

Comparative Experiment 1 (CE-1)

The hydrogenation of Example 1 is repeated, with the exception that only the dialdehyde feed containing 4 weight percent water is used and no additional water and recycle stream are supplied to the hydrogenation reactor. Isopropyl alcohol is added at 15 weight percent to ensure a feasible processing viscosity of the product, else the feed would have an unsuitable viscosity for processing. The 4 weight percent water is equivalent to 2 mole equivalents water per mole equivalent dialdehyde or 1 mole water per mole formyl substituent. The experiment is run for 400 hours with product sampling. Results are presented in Table 1. When Example 1 is compared with Comparative Experiment 1, it is seen that the addition of water at 20 weight percent in accordance with this invention not only decreases intra-molecular formation of hemiacetal (e.g., 1,3-hemi-acetal as shown below in Formula X), but decreases significantly dimer and trimer oligomer formation from the dialdehyde self-condensation. Concurrently, the dialdehyde raw material efficiency is increased by 1.8 percent in this embodiment of the invention.

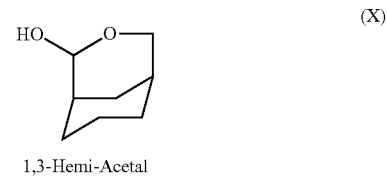

1,3-Hemi-Acetal

EMBODIMENTS OF THE INVENTION

Embodiments of the invention include the following:

1. A process for the hydrogenation of an aliphatic dialdehyde to prepare an aliphatic diol comprising contacting one or more aliphatic dialdehydes in a liquid phase with hydrogen in the presence of a hydrogenation catalyst in a hydrogenation zone, and in the presence of water in an amount equal to or greater than 10 weight percent, based on the weight of the total liquid feed to the hydrogenation zone, the contacting being conducted under reaction conditions sufficient to prepare one or more corresponding aliphatic diols.

2. A process of preparing one or more aliphatic diols comprising:

(a) contacting in a hydroformylation zone an olefinically-unsaturated aliphatic aldehyde with carbon monoxide and hydrogen in the presence of a transition metal-organophosphorus ligand complex catalyst and, optionally, free organophosphorus ligand under hydroformylation conditions sufficient to prepare a hydroformylation product composition comprising one or more aliphatic dicarboxaldehydes, the transition metal-organophosphorus ligand complex catalyst, and optionally, free organophosphorus ligand;

(b) mixing in an extraction zone the hydroformylation product composition with water and, optionally, a nonpolar solvent under conditions sufficient to obtain by phase separation a nonpolar phase comprising the transition metal-organophosphorus ligand complex catalyst, optionally, free organophosphorus ligand, and optionally, the nonpolar solvent and a polar phase comprising water and the one or more aliphatic dicarboxaldehydes;

(c) feeding at least a portion the polar phase from extraction step (b) comprising water and the one or more aliphatic dialdehydes, with or without an additional co-feed of water, into a hydrogenation zone, in an amount of water equal to or greater than 10 weight percent based on the weight of the total liquid feed to the hydrogenation zone, and hydrogenating the aliphatic dicarboxaldehyde(s) in a liquid phase with hydrogen in the presence of said water and in the presence of a hydrogenation catalyst, under hydrogenation conditions sufficient to prepare one or more corresponding aliphatic diols.

3. Any one of the aforementioned embodiments wherein the aliphatic dialdehyde comprises an alicyclic dialdehyde, more preferably, a monocyclic $C_6$-$C_{16}$ aliphatic dicarboxaldehyde, most preferably, a mixture of cis/trans-(1,3)(1,4)-cyclohexane dicarboxaldehydes.

4. Any one of the aforementioned embodiments wherein the monocyclic $C_6$-$C_{16}$ aliphatic dicarboxaldehyde is represented by the following formula (I):

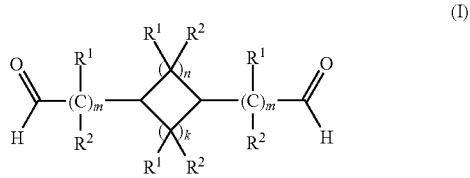

(I)

wherein each $R^1$ is independently selected from hydrogen, hydroxy, and $C_1$-$C_6$ monovalent hydrocarbyl radicals, preferably, hydrogen and $C_1$-$C_3$ alkyl radicals; wherein each $R^2$ is independently selected from hydrogen, hydroxy, and $C_1$-$C_6$ monovalent hydrocarbyl radicals, preferably, hydrogen and $C_1$-$C_3$ alkyl radicals; each n is an integer from 0 to about 6, preferably, from 0 to 3, more preferably, 2; each k is an integer from 0 to about 6, preferably, from 0 to 3, more preferably, 2; n+k is greater than 2; and each m is independently an integer from 0 to about 3, preferably, 0 or 1; and wherein if n or k is 0, then the two chains of m carbon atoms are directly linked to each other; and further wherein $R^1$ and $R^2$ can be substituted with one or more substantially inert substituents that do not interfere with the process of this invention, non-limiting examples of which include hydroxy, alkyl, aryl, aralkyl, and alkaryl radicals, wherein the aforementioned organic radicals preferably comprise from 1 to about 8 carbon atoms, preferably, hydroxy.

5. Any one of the aforementioned embodiments wherein the monovalent aliphatic dicarboxaldehyde is selected from cis-1,3-cyclohexane dicarboxaldehyde, trans-1,3-cyclohexane dicarboxaldehyde, cis-1,4-cyclohexane dicarboxaldehyde, trans-1,4-cyclohexane dicarboxaldehyde, cis-1,3-cyclooctane dicarboxaldehyde, trans-1,3-cyclooctane dicarboxaldehyde, cis-1,4-cyclooctane dicarboxaldehyde, trans-1,4-cyclooctane dicarboxaldehyde, cis-1,5-cyclooctane dicarboxaldehyde, and trans-1,5-cyclooctane dicarboxaldehyde, and mixtures of the aforementioned compounds 6. Any one of the aforementioned embodiments wherein the monocyclic $C_6$-$C_{16}$ aliphatic dicarboxyaldehyde comprises an isomeric mixture of cis/trans-(1,3)-cyclohexanedicarboxaldehyde and cis/trans-(1,4)-cyclohexanedicarboxaldehyde, and wherein optionally the isomeric mixture comprises from about 50 to 60 percent 1,3-isomer and from about 40 to 50 percent 1,4-isomer, by weight.

7. Any one of the aforementioned embodiments wherein the aliphatic dialdehyde comprises one or more impurity carboxylic acids, acetals, hemiacetals, enol ethers, saturated ethers, organophosphites and degradation products thereof, and self-condensation heavies including dimers, trimers, and higher oligomers.

8. Any one of the aforementioned embodiments wherein the aliphatic dialdehyde comprises from about 0.005 to about 5 weight percent each of acetals, hemiacetals, and other heavies (including dimers, trimers and higher oligomers), calculated on the total weight of the aliphatic dialdehyde.

9. Any one of the aforementioned embodiments wherein the aliphatic dialdehyde is prepared by hydroformylation of an unsaturated aliphatic monocarboxaldehyde, which is prepared in a Diels Alder condensation reaction of a diene with a dienophile, such as an unsaturated aldehyde.

10. Any one of the aforementioned embodiments wherein the metal-organophosphorus ligand complex catalyst employable in the hydroformylation process to prepare the aliphatic dialdehyde comprises a metal-organophosphite ligand complex catalyst.

11. Any one of the aforementioned embodiments wherein the metal of the metal-ligand complex catalyst of the hydroformylation process for preparing the aliphatic dialdehydes comprises a transition metal selected from Groups 8, 9 and 10 of the Periodic Table, preferably, rhodium, cobalt, iridium and ruthenium, more preferably rhodium, cobalt and ruthenium, and most preferably, rhodium.

12. Any one of the aforementioned embodiments wherein the organomonophosphite ligand comprises organophosphites of Formula III:

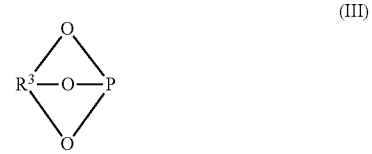

(III)

wherein $R^3$ represents a substituted or unsubstituted trivalent hydrocarbon radical containing from about 4 to 40 carbon atoms, such as trivalent acyclic and trivalent cyclic radicals, 13. Any one of the aforementioned embodiments wherein the organomonophosphite is represented by Formula IV:

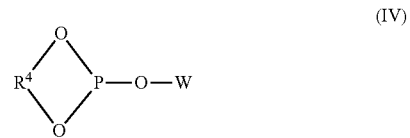

(IV)

wherein $R^4$ represents a substituted or unsubstituted divalent hydrocarbon radical containing from about 4 to 40 carbon atoms and W represents a substituted or unsubstituted monovalent hydrocarbon radical containing from 1 to about 18 carbon atoms.

14. Any one of the aforementioned embodiments wherein the organophosphite is a diorganophosphite of Formula V:

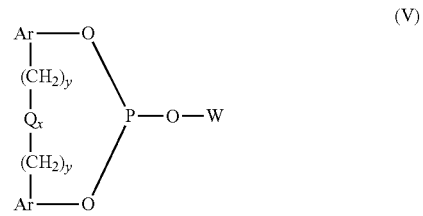

(V)

wherein W represents a substituted or unsubstituted monovalent hydrocarbon radical containing from 1 to about 18 carbon atoms, each Ar is the same or different and represents a substituted or unsubstituted divalent aryl radical, each y is the same or different and is a value of 0 or 1, Q represents a divalent bridging group selected from —C($R^5$)$_2$—, —O—, —S—, —N$R^6$—, —Si($R^7$)$_2$— and —CO, wherein each $R^5$ is the same or different and is selected from hydrogen, alkyl radicals having from 1 to 12 carbon atoms, phenyl, tolyl, and anisyl, $R^6$ represents hydrogen or an alkyl radical of from 1 to 10 carbon atoms, preferably, methyl, each $R^7$ is the same or different and represents hydrogen or an alkyl radical having from 1 to about 10 carbon atoms, preferably, methyl, and x is a value of 0 or 1.

15. Any one of the aforementioned embodiments wherein the organophosphite is a triorganophosphite represented by Formula VI:

wherein each $R^8$ is the same or different and is a substituted or unsubstituted monovalent hydrocarbon radical of from 1 to 24 carbon atoms, preferably, alkyl, cycloalkyl, aryl, alkaryl, or aralkyl.

16. Any one of the aforementioned embodiments wherein the organophosphite is tris-(2,4-di-tert-butylphenyl)phosphite of Formula VII:

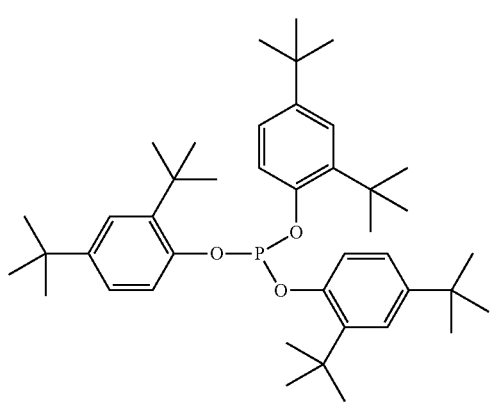

17. Any one of the aforementioned embodiments wherein the amount of metal-ligand complex catalyst present in the reaction fluid of the hydroformylation process to prepare the aliphatic dialdehyde ranges from about 10 parts per million to about 1000 parts per million, more preferably from about 10 to 500 parts per million of metal, and even more preferably from 25 to 350 parts per million of metal, calculated as free metal in the hydroformylation reaction fluid.

18. Any one of the aforementioned embodiments wherein free organophosphite ligand is present in the hydroformylation reaction fluid in a quantity from about 0.1 mole to about 100 moles of free ligand per mole of metal in the hydroformylation reaction fluid, preferably, from about 1 to about 50 moles of ligand, and more preferably from about 1.1 to about 4 moles of ligand, per mole of metal present in the reaction fluid; said amounts of ligand being the sum of both the amount of ligand that is bound (complexed) to the metal and the amount of free (non-complexed) ligand present 19. Any one of the aforementioned embodiments wherein the hydroformylation process to prepare the aliphatic dialdehyde is conducted at a $H_2$:CO molar ratio of gaseous hydrogen to carbon monoxide ranging from about 1:10 to 100:1, the more preferred molar ratio being from about 1:10 to about 10:1.

20. Any one of the aforementioned embodiments wherein the hydroformylation process to prepare the aliphatic dialdehyde is conducted at a reaction temperature greater than about −25° C., more preferably, greater than about 50° C., but less than about 200° C., and preferably, less than about 120° C.

21. Any one of the aforementioned embodiments wherein the hydroformylation process to prepare the aliphatic dialdehyde is conducted at a total gas pressure comprising hydrogen, carbon monoxide and olefinic reactant (unsaturated carboxyaldehyde) ranging from about 1 psia (6.8 kPa) to about 10,000 psia (68.9 MPa), preferably, from about 1 psia (6.8 kPa) to less than about 2,000 psia (13,800 kPa), and more preferably, from about 1 psia (6.8 kPa) to less than about 500 psia (3,450 kPa).

22. Any one of the aforementioned embodiments wherein the hydroformylation process to prepare the aliphatic dialdehyde is conducted at a carbon monoxide partial pressure ranging from about 1 psia (6.8 kPa) to about 1000 psia (6,900 kPa), and preferably, from about 3 psia (20.7 kPa) to about 800 psia (5,516 kPa); while the hydrogen partial pressure is ranging from about 5 psia (34.5 kPa) to about 500 psia (3,450 kPa), and preferably, from about 10 psia (68.0 kPa) to about 300 psia (2,070 kPa).

23. Any one of the aforementioned embodiments wherein the extraction step (b) uses water as the preferred extraction solvent, optionally, in combination with a non-aqueous polar solvent, preferably a $C_{1-6}$ alkanol, such as methanol, ethanol, propanol, and butanol.

24. Any one of the aforementioned embodiments wherein the extraction step (b) is conducted with a quantity of water and non-aqueous polar solvent(s) comprising greater than about 10 percent up to about 20 percent, by weight, based on the weight of the total feed to the extractor.

25. Any one of the aforementioned embodiments wherein the extraction step (b) is conducted using a quantity of water and non-aqueous polar solvent(s) comprising greater than about 20 percent, more preferably, greater than about 50 percent, up to about 95 percent, based on the weight of the total feed to the extraction step; more preferably, the water level exceeds 50 percent, and most preferably ranges between about 80 and 95 percent, by weight, based on the weight of the total feed to the extractor.

26. Any one of the aforementioned embodiments wherein the extraction step (b) is conducted in presence of one or more nonpolar solvents, such as liquid alkanes, cycloalkanes, alkenes, aromatic hydrocarbons, and mixtures thereof, illustrative species of which include, without limitation, 2,2-dimethylpropane, 2,2-dimethylbutane, pentane, isopropyl ether, hexane, heptane, octane, nonane, decane, isobutyl isobutyrate, tributyl heptyl ketone, diisobutyl ketone, cyclopentane, cyclohexane, isobutylbenzene, n-nonylbenzene, n-octylbenzene, p-xylene, ethylbenzene, 1,3,5-trimethylbenzene, m-xylene, toluene, o-xylene, decene, dodecene, and tetradecane.

27. Any one of the aforementioned embodiments wherein the hydrogenation is conducted using a quantity of water greater than about 4 mole equivalents of water per mole equivalent of aliphatic dicarboxaldehyde or greater than about 2 mole equivalents of water per mole equivalent formyl substituent.

28. Any one of the aforementioned embodiments wherein the hydrogenation catalyst is provided as a solid fixed bed, preferably, as precipitated, pelletized, shaped, or extruded particles, or alternatively in a batch reactor, fluidized bed reactor, trickle bed reactor, single or multiple pass reactor.

29. Any one of the aforementioned embodiments wherein the hydrogenation catalyst comprises one or more metals selected from Groups 6, 7, 8, 9, 10, 11, and 12 of the Periodic Table, preferably, Groups 6, 10, and 11, more preferably, chromium, nickel, copper, palladium, platinum, and mixtures thereof, optionally, affixed to a carrier or support, such as aluminum oxide, silicon oxide, titanium oxide, an aluminosilicate, carbon.

30. The aforementioned embodiment wherein in the hydrogenation catalyst, loading of the total catalytic metal(s) onto the carrier or support ranges from about 0.01 weight percent up to about 20 weight percent.

31. Any one of the aforementioned embodiments wherein the hydrogenation catalyst comprises materials and/or stabilizers that promote and/or stabilize the hydrogenation reaction to the desired aliphatic diols, including without limit, alkali metal and alkaline earth metal oxides and alkali metal and alkaline earth metal hydroxides.

32. Any one of the aforementioned embodiments wherein a preferred hydrogenation catalyst comprises nickel supported on alumina.

33. Any one of the aforementioned embodiments wherein a preferred hydrogenation catalyst excludes sulfactive hydrogenation catalysts, such as, Group 6, 7, 8, 9, 10, 11, and 12 sulfides, preferably, molybdenum sulfide, tungsten sulfide, and nickel sulfide.

34. Any one of the aforementioned embodiments wherein in the hydrogenation the molar ratio of hydrogen to moles of carbonyl (formyl) groups is greater than 1.3:1, more preferably, greater than about 1.5:1, preferably, less than about 10:1, and more preferably less than about 5:1, and even more preferably, less than about 3:1.

35. Any one of the aforementioned embodiments wherein the hydrogenation is conducted at a temperature greater than about 40° C., preferably, greater than about 70° C., and less than about 200° C., preferably, less than about 150° C.

36. Any one of the aforementioned embodiments wherein the hydrogenation is conducted at a hydrogen pressure greater than about 3 bar (300 kPa), and preferably, greater than about 5 bar (500 kPa), and advantageously at a pressure less than about 50 bar (5,000 kPa), and preferably, less than about 30 bar (3,000 kPa).

37. Any one of the aforementioned embodiments wherein the hydrogenation is conducted in a continuous mode of operation, the liquid hourly space velocity of the liquid aliphatic dialdehyde feed, containing at least some concentration of water carry-over from the extraction process, advantageously ranges from about 0.01 cm$^3$ liquid feed per cm$^3$ catalyst per hour (h$^{-1}$) to about 100 h$^{-1}$.

38. Any one of the aforementioned embodiments wherein the $C_6$-$C_{16}$ aliphatic diol is represented by the following Formula (VIII):

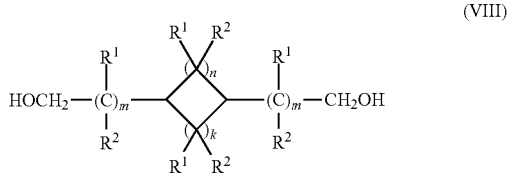

(VIII)

wherein each $R^1$ is independently selected from hydrogen, hydroxy, and $C_1$-$C_6$ monovalent hydrocarbyl radicals, preferably, hydrogen and $C_1$-$C_3$ alkyl radicals; each $R^2$ is independently selected from hydrogen, hydroxy, and $C_1$-$C_6$ hydrocarbyl radicals, preferably, hydrogen and $C_1$-$C_3$ alkyl radicals; n is an integer from 0 to about 6, preferably, from 0 to 3, more preferably, 2; k is an integer from 0 to about 6, preferably, from 0 to 3, more preferably, 2; n+k is greater than 2; and each m is independently an integer from 0 to about 3, preferably, 0 or 1; and if n or k is 0, then the two chains of m carbon atoms are directly linked; and further wherein $R^1$ and $R^2$ can optionally be substituted with one or more substantially inert substituents, such as alkyl, aryl, aralkyl, and alkaryl, and hydroxy, wherein the aforementioned organic substituents contain from 1 to about 8 carbon atoms.

39. Any one of the aforementioned embodiments wherein the $C_6$-$C_{16}$ aliphatic diol comprises an isomeric mixture of cis/trans-(1,3)-cyclohexanedimethanol and cis/trans-(1,4)-cyclohexanedimethanol.

40. Any one of the aforementioned embodiments wherein the amount of water in the hydrogenation process is greater than about 15 weight percent, even more preferably equal to or greater than about 20 and less than about 95 weight percent, based on the weight of the total liquid feed to the hydrogenation zone.

41. Any one of the aforementioned embodiments wherein the yield of aliphatic diol obtained from the hydrogenation process is increased by about 1.5 to about 2.0 weight percent, as compared to a similar process using a quantity of water less than 10 weight percent.

What is claimed is:

1. A process for the hydrogenation of an aliphatic dialdehyde to an aliphatic diol comprising contacting one or more aliphatic dialdehydes in a liquid phase with hydrogen in the presence of a hydrogenation catalyst in a hydrogenation zone, and in the presence of water in an amount equal to or greater than 10 weight percent, based on the weight of the total liquid feed to the hydrogenation zone, the contacting being conducted under reaction conditions sufficient to prepare one or more corresponding aliphatic diols.

2. The process of claim 1 wherein the one or more aliphatic dialdehydes comprise one or more $C_6$-$C_{16}$ alicyclic dicarboxaldehydes.

3. The process of claim 1 wherein the one or more $C_6$-$C_{16}$ alicyclic dicarboxaldehydes are each represented by the following formula:

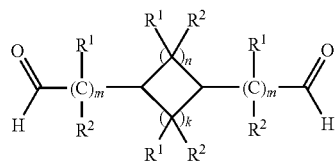

wherein each $R^1$ is independently selected from hydrogen, hydroxy, and $C_1$-$C_6$ monovalent hydrocarbyl radicals, each $R^2$ is independently selected from hydrogen, hydroxy, and $C_1$-$C_6$ monovalent hydrocarbyl radicals, each n is an integer from 0 to about 6, each k is an integer from 0 to about 6, n+k is greater than 2, and each m is independently an integer from 0 to about 3; the selection of $R^1$; $R^2$, k, m, n being such that the total number of carbon atoms does not exceed 16.

4. The process of claim 1 wherein the one or more aliphatic dialdehydes are selected from cis-1,3-cyclohexane dicarboxaldehyde, trans-1,3-cyclohexane dicarboxaldehyde, cis-1,4-cyclohexane dicarboxaldehyde, trans-1,4-cyclohexane dicarboxaldehyde, cis-1,3-cyclooctane dicarboxaldehyde, trans-1,3-cyclooctane dicarboxaldehyde, cis-1,4-cyclooctane dicarboxaldehyde, trans-1,4-cyclooctane dicarboxaldehyde, cis-1,5-cyclooctane dicarboxaldehyde, and trans-1,5-cyclooctane dicarboxaldehyde, and mixtures thereof.

5. The process of claim 1 wherein the hydrogenation catalyst is selected from one or more metals of Groups 6, 7, 8, 9, 10, 11, and 12 of the Periodic Table, and mixtures thereof, optionally supported on a carrier or support.

6. The process of claim 1 wherein the hydrogenation catalyst is selected from chromium, nickel, copper, palladium, platinum, and mixtures thereof.

7. The process of claim 1 wherein the hydrogenation catalyst comprises nickel supported on an alumina carrier.

8. The process of claim 1 wherein the process is conducted at a temperature greater than about 40° C. and less than about 200° C. and at a hydrogen pressure greater than about 3 bar (300 kPa) and less than about 50 bar (5,000 kPa).

9. The process of claim 1 wherein the molar ratio of hydrogen to carbonyl (formyl) groups in the aliphatic dialdehyde is greater than about 1.3:1 and less than about 10:1.

10. The process of claim 1 wherein the quantity of water ranges from greater than 20 percent to less than 95 percent, by weight, based on the total liquid feed to the hydrogenation process.

11. The process of claim 1 wherein the aliphatic diol is an aliphatic monocyclic diol.

12. The process claim 1 wherein the aliphatic monocyclic diol is represented by the following formula:

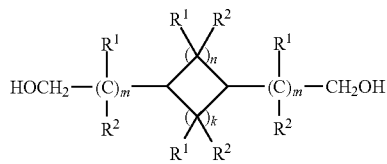

wherein each $R^1$ is independently selected from hydrogen, hydroxy, and $C_{1-6}$ monovalent hydrocarbyl radicals, each $R^2$ is independently selected from hydrogen, hydroxy, and $C_{1-6}$ monovalent hydrocarbyl radicals, n is an integer from 0 to about 6, k is an integer from 0 to about 6; n+k is greater than 2, and each m is independently an integer from 0 to about 3; the selection of $R^1$, $R^2$, k, m, n being such that the total number of carbon atoms does not exceed 16.

13. The process of claim 1 wherein the aliphatic diol comprises one or more isomers of cis/trans-(1,3)(1,4)-cyclohexane dimethanol.

14. The process of claim 1 wherein moles of water relative to moles of aliphatic dialdehyde fed to the hydrogenation zone are greater than 4/1 (or moles of water per mole equivalent of formyl substituent is greater than 2/1).

15. The process of claim 1 wherein the yield of aliphatic diol obtained from the hydrogenation process is increased by about 1.5 to about 2.0 weight percent, as compared to a similar process using a quantity of water less than 10 weight percent.

16. A process of preparing one or more aliphatic diols comprising:
(a) contacting in a hydroformylation zone an olefinically-unsaturated aliphatic aldehyde with carbon monoxide and hydrogen in the presence of a transition metal-organophosphorus ligand complex catalyst and, optionally, free organophosphorus ligand under hydroformylation conditions sufficient to prepare a hydroformylation product composition comprising one or more aliphatic dicarboxaldehydes, the transition metal-organophosphorus ligand complex catalyst, and optionally, free organophosphorus ligand;
(b) mixing in an extraction zone the hydroformylation product composition with water and, optionally, a nonpolar solvent under conditions sufficient to obtain by phase separation a nonpolar phase comprising the transition metal-organophosphorus ligand complex catalyst, optionally, free organophosphorus ligand, and optionally, the nonpolar solvent and a polar phase comprising water and the one or more aliphatic dicarboxaldehydes;
(c) feeding at least a portion of the polar phase from extraction step (b) comprising water and the one or more aliphatic dicarboxaldehydes, with or without an additional co-feed of water, into a hydrogenation zone in an amount of water equal to or greater than 10 weight percent, based on the weight of the total liquid feed to the hydrogenation zone, and hydrogenating the aliphatic dicarboxaldehyde(s) in a liquid phase in the presence of said water with hydrogen in the presence of a hydrogenation catalyst under hydrogenation conditions sufficient to prepare one or more corresponding aliphatic diols.

17. The process of claim 16 wherein the extraction step (b) is conducted with water in an amount greater than 10 percent up to about 20 percent, by weight, based on the weight of the total feed to the extractor.

18. The process of claim 16 wherein the extraction step (b) is conducted with water in an amount greater than 50 and less than 95 weight percent, based on the weight of the total feed to the extractor.

19. The process of claim 16 wherein moles of water relative to moles of aliphatic dicarboxaldehyde(s) fed to the hydrogenation zone are greater than 4/1 (or moles of water per mole equivalent of formyl substituent is greater than 2/1).

* * * * *